United States Patent [19]

Jones

[11] 3,987,548
[45] Oct. 26, 1976

[54] BITE REGISTRATION TRAY AND COMBINATION THEREOF WITH BIB

[76] Inventor: Russell J. Jones, 13804 Lake Shore Drive, Bratenahl, Ohio 44110

[22] Filed: July 3, 1975

[21] Appl. No.: 593,104

[52] U.S. Cl. .................................................. 32/17
[51] Int. Cl.² ........................................ A61C 9/00
[58] Field of Search ........................................ 32/17

[56] References Cited
UNITED STATES PATENTS

| 3,574,259 | 4/1971 | Jones | 32/17 |
| 3,822,473 | 7/1974 | Jones | 32/17 |

Primary Examiner—Robert Peshock
Attorney, Agent, or Firm—John Harrow Leonard

[57] ABSTRACT

A bite tray for taking a bite registration impression of the posterior teeth of a full set of teeth includes a bib and frame so shaped and arranged that, in the absence of some occluding posterior teeth, beginning with the rearmost occluding teeth and continuing progressively forwardly therefrom as occluding corresponding teeth are absent, the frame and bib can be adjusted and manipulated forwardly to include in the bite registration impression of not only the remaining posterior teeth but also an impression of the incisors and progressively more of the labial teeth without striking the labial surfaces of the jaw or of the labial teeth. The frame is so proportioned and the bib so manipulatable that they make possible the taking of such bite impressions in true centric occlusion of the teeth.

8 Claims, 7 Drawing Figures

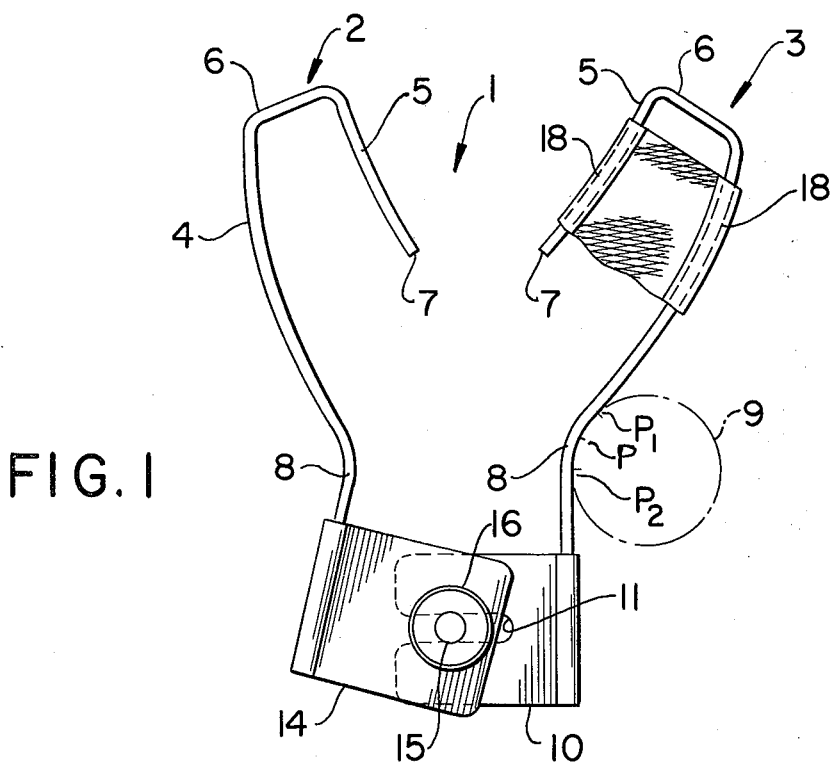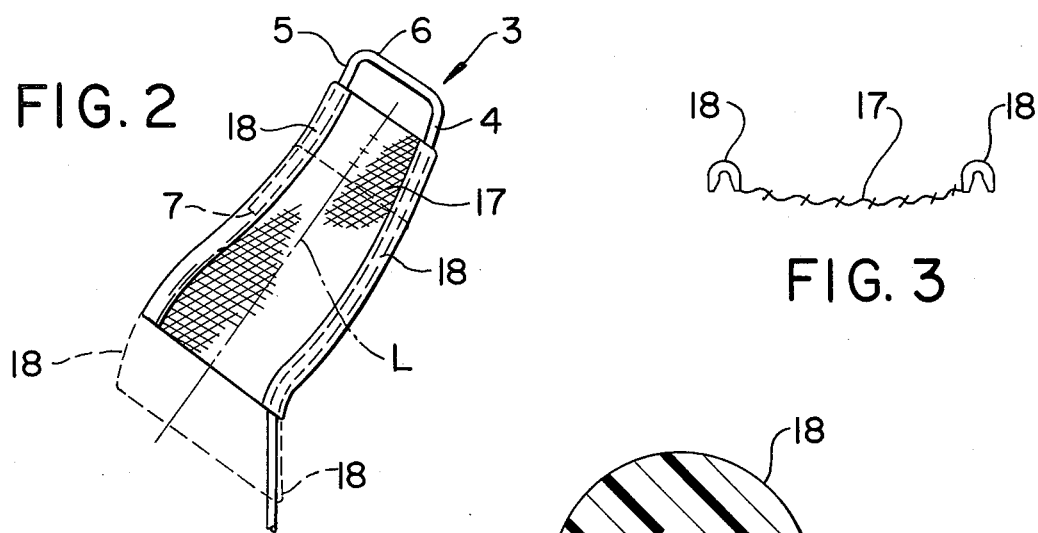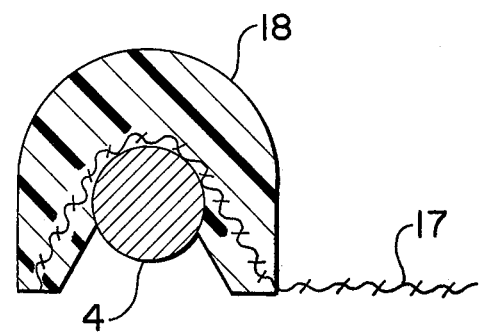

3,987,548

BITE REGISTRATION TRAY AND COMBINATION THEREOF WITH BIB

BACKGROUND OF THE INVENTION

1. Field of Invention

Bite impression trays.

2. Description of the Prior Art

This invention relates to a bite tray which is an improvement on the structures disclosed in my United States Letters Pat. No. 2,713,202 of July 19, 1955, No. 3,822,473 of July 9, 1974, and in my copending application Ser. No. 460,430, filed Apr. 12, 1974, and entitled Bib and Combination Thereof With Bite Tray, now U.S. Pat. No. 3,903,602, of Sept. 9, 1975. More particularly my invention is an improvement in the frame of the bite tray disclosed in my above identified patents and its interrelation with the bib of my above copending application.

As described in my U.S. Pat. No. 3,822,473, two bite tray frames are disclosed, each being in the form of a single length of stiff, resilient wire bent to provide a buccal side frame member, a lingual side frame member spaced laterally therefrom, and an intermediate or rear frame member of which the opposite ends connect with the rear ends of the buccal frame member and the lingual frame member, respectively. A portion of the wire extends endwise beyond the opposite or forward end of the buccal frame member and provides a handle. The opposite or forward end of the lingual frame member is left free and unconnected in any way to the buccal frame member.

Companion or mating tabs are provided on the outer end portions of the handles, respectively, of the two frames. The tabs are interfitted and connected so that they support the handles for swinging toward and away from each other in a common plane and for bodily movement transversely relative to each other in that plane so that the frame can be adjusted for different sizes and shapes of dental arches. The interfitting tabs can be clamped together in the adjusted positions and, when so clamped, can be held readily between the thumb and forefinger for introducing into a patient's mouth.

Each frame carries a bib. Each bib is provided at its lateral margins with channel members which are adapted for snap fastening engagement with the buccal frame member and the lingual frame member, respectively, of an associated frame, so as to hold the bib in bridging relation to the space between the buccal and lingual frame members and for sliding of the channels of the bib lengthwise of their associated buccal and lingual frame members to different adjusted positions lengthwise of the lingual and buccal frame members, in which positions they are retained by frictional binding.

The channel members are sufficiently rigid so that insofar as they may extend beyond the free ends of the lingual frame members their overhanging portions are adequate to be self-supporting and to support the overhanging portion of the bib with the necessary quantity of impression paste thereon.

The adjustment of the tray to fit different dental arches of which a bite registration impression is to be taken proceeds by trial and error. When adjusted for the particular arches, and with bibs is place and supporting proper charges of impression paste, the frame is inserted in the open mouth in a position to take the bite registration impression.

The relation of the buccal and lingual frame members of each of the above frames to each other and their relation, in turn, to their associated handles, limited substantially the possibilities of placement of the frames in those optimum forward positions in the mouth desirable in those cases in which the rearmost upper and lower posterior teeth, or two or three occluding teeth forwardly therefrom are missing. In such instances, the number of registration impressions of occluding teeth is very limited, and yet it is desirable that as many occluding teeth as possible be included in the bite registration impression so that the castings of dental impressions to be used for partial or full dental plates can be mounted in proper or true centric occlusion in the articulator in which the impressions are mounted and adjusted subsequently for constructing proper dentures. With the previous frames, the lengths of the lingual frame member of each frame is so long relative to the buccal frame member that the lingual frame member would strike the interior of the dental arch at the lingual surface of the labial teeth upon slight movement of the frame to desirable more forward adjusted positions. Furthermore, the handles were of such length relative to the buccal and lingual frame members that it was difficult for the dentist to hold the frame and bibs substantially coplanar with the occusion plane of the teeth while he held the jaws in true centric relation for centric occlusion.

SUMMARY

In the present invention the bib is constructed so that it can properly support the paste without an appreciable deflection even with substantial overhang of the bib relative to the lingual frame member. The lingual frame member is shortened appreciably relative to the buccal frame member so that the entire frame can be moved forwardly in the mouth to a greater degree than the prior frames, so as to include in the impression the cuspids and the anterior teeth in those cases in which such a desirable for obtaining a good bite registration impression. Further, the handles of the frames are related in length to the associated frame members and to the structure of the human hand so that the bite registration tray can be held substantially in the plane of occlusion of the upper and lower dental arches and inserted between the dental arches while the lower jaw is held by the operator in centric relation and close to closed position.

These features assure a bite impression as extensive as is possible for the teeth present in the particular arches, and with the jaws in true centric relation.

Various other specific objects and advantages will become apparent from the following description wherein reference is made to the drawing.

BRIEF DESCRIPTION OF THE DRAWINGS

FIG. 1 is a top plan view of an impression tray embodying the principles of the present invention, the frames being shown in full line and part of one bib being shown fragmentarily on one frame for clearness in illustration;

FIG. 2 is an enlarged fragmentary plan view of one of the frames illustrating adjusted positions of the bib;

FIG. 3 is an end view of one of the bibs used with the frame;

FIG. 4 is an enlarged cross sectional view of a portion of the bib illustrated in FIG. 3, showing the manner in which the bib is fastened to the frame;

PREFERRED EMBODIMENT

Figure 5:
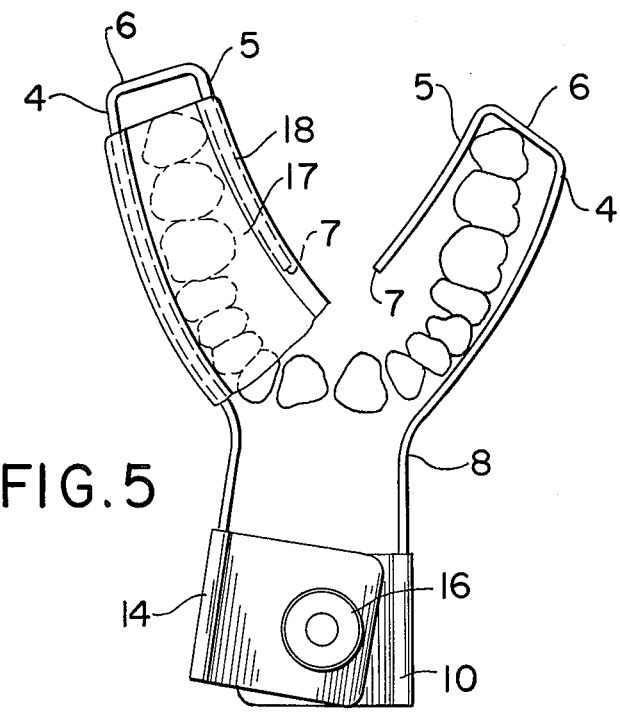
FIG. 5 is a diagrammatic top plan view showing the relation of the frame to a dental arch with a full set of teeth.

Referring first to FIG. 1, the bite impression tray, indicated generally at 1, comprises a left frame 2 and a right frame 3. These frames are identical, except for the finger tabs hereinafter described, and therefore only the right hand frame 3 will be described in detail.

The frame 3 is in the form of a single length of relatively stiff, resilient wire bent to provide a buccal frame member 4 and a lingual frame member 5 joined at their rear ends by an intermediate or rear frame member 6. The forward end of the lingual frame member 5, as indicated at 7, is free and can be moved toward and away from the buccal frame member 4 by lateral flexure of the frame members. A portion of the wire extends endwise forwardly from the forward end of the buccal frame member 4 and provides a handle 8 which preferably is straight.

The buccal and lingual frame members of each frame are generally parallel with each other and coplanar, and are slightly curvilinear and concave toward the other frame. The curved buccal frame member 4 and handle 8 are joined by a transition curve, indicated generally at 9, which has a radius of about one half inch and merges with the curve of the buccal frame member 4 and with the handle 8 at points of tangency indicated at $P_1$ and $P_2$ in FIG. 1.

The forwardmost end portions of the handles 8 are connected to companion mating holding tabs. The right hand frame 3 is connected to a tab 10 in the form of a flat sheet of metal having one margin bent around and soldered to the forward end portion of the handle 8. The tab 10 has an elongated slot 11 extending generally normal to the plane of the tab. The left hand frame 2 has a similar tab 14 which is in the form of an elongated flat sheet of metal bent midway between its ends so as to embrace the handle 8 of the left hand frame 2, and is soldered to the handle so as to leave two wings extending from the handle in slightly spaced face to face relation. The tab 10 is slidably and snugly accommodated between the wings of the tab 14. The tab 14 carries a bolt 15 and a clamping nut 16. The tabs are otherwise preferably of the same shape so that the tab 10 can be slid between the wings of the tab 14 with the bolt disposed in the notch 11 and thus adjusted to move the handles 8 to different positions bodily transversely of the tray. The tabs can be rocked relative to each other about the axis of the bolt 15 and, in each instance, clamped in adjusted rocked position. This provides a somewhat universal adjustment of the positions of the frames 2 and 3 of the tray relative to each other in a common plane as required to fit in the optimum position in the mouth of a patient. Each frame supports a bib 17.

The structure thus far described is quite similar to that disclosed in my above U.S. Pat. No. 2,713,202.

However, in the present invention, the lingual frame member 5 is considerably shorter than the buccal frame member 4, measured from the rear frame member 6 to the point of tangency $P_1$ of the buccal frame member. Furthermore, the handle 8 is much shorter than the corresponding handle of the frame of said patent. The tabs 10 and 14 may be essentially the same dimension lengthwise of the tray as those of the patent.

Since the proportions of the lengths of the buccal and lingual frames and of the handles are important, the dimensions of these and other parts of the frames, which distinguish from the earlier disclosure and which are necessary for obtaining the advantages of the present invention, are set forth.

In the preferred embodiment of the invention, the wire is from three sixty-fourths to one sixteenth inches in diameter. The lingual frame member 5 is about one-five-sixteenth inches long, measured from the forward side of the rear frame member 6 to the free end 7 of the lingual frame member. The buccal frame member is about 2 inches long, measured from the forward side of the rear frame member 6 to the point of tangency $P_1$ of the curve 9 joining the handle 8 and the buccal frame member 4. The length of this intermediate curve 9, between the point of tangency $P_1$ and the point of tangency $p_2$, is about three eighths of an inch, and the length of the portion of the handle between the point of tangency $p_2$ and the rearmost edge of the tab 10 is about nine sixteenths of an inch. The tab length is about 1 inch. The radius of curvature of the buccal and lingual frame members is about 3 and 11/16 inches, being greater than in the frames of my above patents.

The bib has an overall length of about 2 inches. As illustrated in FIG. 2, it normally is mounted on its associated frame so that the rear edge of the bib is about one fourth of an inch forwardly from the rear frame member 6, as shown in solid lines. On an intermediate construction line L some of the many different adjusted positions of the bib forwardly from the rear frame 6 are indicated, such for examples, as three eighths of an inch, one half inch, five eighths of an inch, and finally three fourths of an inch which latter is usually the maximum. In these positions, it is apparent that on the lingual frame member 5 the bib in the rearmost position extends forwardly beyond the free end of the lingual frame member about fifteen sixteenths of an inch and on the buccal frame member it terminates forwardly just about at the point of tangency $P_2$. On the other hand, if the bib is adjusted forwardly so that the rear edge is three fourths of an inch from the rear frame member, then the overhang of the bib from the free end 7 of the lingual frame member 5 is about one and seven-sixteenths inches, which is about the maximum forwardmost position.

Considering the point of intersection P of the handle and curve of the buccal frame member 4 is about midway between the two points of tangency $P_1$ and $P_2$ and assuming the lenght of the buccal frame member 4 and handle are measured to this point P, the ratio of the length of the handle to that of the buccal frame member is about 80 percent. The ratio of the length of the lingual frame member to the buccal frame member is about 60 percent, so that the lingual frame member 5 is approximately frame ½ to ⅔ the length of the buccal frame member 4. The length of the bib relative to the buccal frame member is about 100 percent and relative to the lingual frame member is about 150 percent. The overhang of the bib relative to the free end 7 of the lingual frame member 5 ranges from about 1 inch to 1 and ¾ inches, depending on the adjusted position of the bib.

As disclosed generally in my above identified application and as illustrated specifically in FIGS. 3 and 4, the bib comprises a strip of unwoven, felted material which is embedded at its lateral margins in the channels 18 of suitable plastic material which is sufficiently rigid to support the bib on the frame while the bib is charged with paste and while in the position of maximum overhang of the bib 17 relative to the free end 7 of the lingual frame member. The plastic is such that it can be cut readily with a knife or lancet so that the impression can be removed from the frames 2 and 3 to permit reuse of the frames.

Referring to FIG. 5, the frame is shown as in a position for a bite registration of a full set of posterior teeth. It does not include the cuspids. When so used the bib 17 is slid forwardly from the rear frame member 6 about one fourth of an inch so as to form a visual space for locating the rear edge of the bib relative to the rearmost edge of the posterior teeth and for assuring that the rear frame member does not engage the teeth. In this position, the forward edge of the bib at the lingual side of the dental arch extends sufficiently forwardly so that the forward edge of the bib may overlie at least part of the adjacent cuspid. However, in many instances, the rearmost of the posterior teeth are missing, and of times also are some adjacent thereto. Yet it is desirable for adjustment of dental impressions properly in an articulator for constructing full or partial plates to have a bite impression of as many occluding teeth as possible. Beginning with the rear tooth and continuing forwardly, if occluding teeth are missing, the frame can be moved forwardly for obtaining the impression of the remaining teeth, especially when one frame only is being used at the time. If there is some symmetry in the loss of teeth from both sides of the mouth, then both frames can be moved forwardly together.

Figure 6:
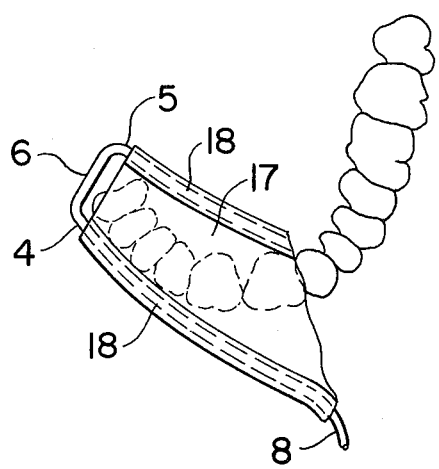
FIG. 6 is a fragmentary view of one of the frames showing the portion of a frame in use for taking a maximum bite impression in a case wherein part of the posterior teeth of a dental arch are missing.

Assuming, however, that only one frame is being used, it is apparent that with the bib in a position one fourth of an inch forwardly of the rear frame, the forward end of the bib is close to the lingual side of the cuspid. However, the free end 7 of the lingual frame is a considerable distance to the rear of the forward end of the bib. This is not particularly important when a bite impression is taken of a full set of teeth. However, as mentioned, and as illustrated in FIG. 6, when quite a number of the posterior teeth are missing, it is desirable that as many teeth as possible be included in the bite registration impression so greater accuracy can be achieved in setting castings of the dental arches in registration in an articulator. To this end, the frame can be moved forwardly a much greater degree than the frame of my patent, due to the much shorter length of the lingual frame member, without the free end 7 of the lingual frame member striking the lingual side of the labial teeth or portion of the arch.

Generally, the rear frame 6 must be kept just to the rear of the rearwardmost remaining posterior tooth. At the same time, it is desirable to let the forward edge of the bib extend as far forwardly as possible to obtain an impression of as many of the remaining teeth as possible even, in some cases, including part or all of the cuspids. The shorter lingual frame members of the present frames permits adjustment of the frame to a much more forward position. The buccal channel of the bib can extend as far as the cuspids or forwardly therebeyond, while the free end 7 of the much shorter lingual frame member 5 remains out of contact with the lingual side of the anterior teeth. With such a relation if the bib 17 were left its full length at the free end 7 of the lingual frame member, the channel 18 would strike the lingual side of the arch, and thus be flexed at its forward portion. As a result, the impression would be taken with the bib 17 in flexed condition. This would distort the resultant registration impressions. For this reason, the channel 18, as mentioned, is made of material which can be cut readily with a knife and consequently, before loading the paste onto the bib 17, with the bib adjusted to the desired forward position, as illustrated in FIG. 6, for obtaining as much impression as possible, the forward end portion of the lingual channel 18 is served so as not to engage the arch and the bib 17 is cut obliquely to its width from the forward end of the remainder of the lingual channel to the maximum forward position of the forward end of the buccal channel. Thus, the impression can be taken of more remaining teeth, including some of the anterior teeth, without the frame member being flexed out of normal position or engaging with the lingual side of the arch. As a result, the maximum number of teeth can be included in the bite registration.

However, another problem is involved in obtaining a proper bite registration, and that is obtaining a bite registration with the jaws in true centricity upon occlusion of the teeth. One of the great difficulties in producing good fitting dentures is in obtaining an accurate bite registration for setting the castings of the teeth and jaws in the articulator and for adjusting them to proper position. If the bite registration has not been taken in the true centric relation of the jaws, then no matter how much adjustment is made in the articulator, the teeth of the dentures cannot be brought to proper registration and partial or full plates made on the basis of the eccentric impression will never fit satisfactorily and feel comfortable. It is absolutely essential in obtaining a proper bite registration that occlusion of the teeth on the paste occurs while the jaws are in true centric relation. The frames of the tray of this invention are proportioned for taking a true centric bite impression.

Figure 7:
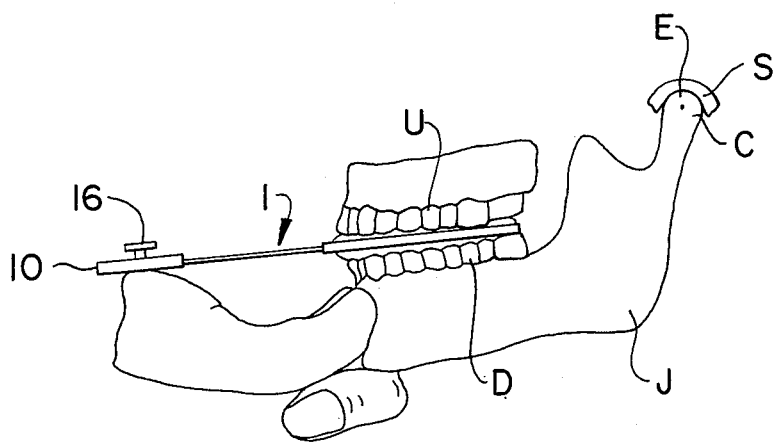
FIG. 7 is a side elevation of the jaws of a human skeleton, showing the manner in which the impression tray is inserted in the mouth and held in proper relation to the teeth while the jaws are held in proper centric relation.

For example, referring to FIG. 7, the upper dental arch is indicated at U and the lower dental at D. The lower jaw J has a condile head C which operates in a cartilaginous socket S in the cranium. Thus, when the jaw is unopposed by anything between the teeth, it can swing about the center E of the condile head C. However, if any resistance to closure is imposed on the jaws by virtue of something between the teeth, the condile head is shifted by the various muscles. This shifting is a reflex action for causing the lower jaw as a whole or at either side to move forwardly and rearwardly somewhat linearly, and to move transversely linearly, and to move in all manner of combinations of such components. The matter is complicated because this movement may not be the same for both condile heads concurrently. The muscles coact to cause a somewhat rotary grinding movement for mastication of food. For example, the masseter, temporal, and internal pterygoid muscles raise and lower the lower jaw and assist an external pterygoid muscle in drawing the lower jaw forward on the upper. The jaw is drawn down and backwardly from this position by the masseter and posterior fibers of the temporal muscle. If resistance to closure occurs at one side of the mouth, the external pterygoid muscle at that side only tends to draw the jaw forwardly, the condile head at the opposite side of the jaw remaining in its original position. It, therefore, becomes important to be sure that the jaws close in true centric relation when taking impressions of the bite, and this requires that the bite impression be taken while the condile heads are centrically disposed in their respective sockets concurrently.

As illustrated in FIG. 7, if resistance occurs between the teeth, and depending upon the type of resistance, the center of the condile head at one side only of the jaw, about which the pivotal action occurs, is drawn upwardly vertically, or to the right or left, or forwardly or rearwardly, while the other of the condile heads remains centric or differently eccentric. Only when both condile heads are in their true centric relation concurrently in their socket in the cranium, is occulsion of the teeth in true centric relation obtained. In view of this the dentist making the impression must press rearwardly and upwardly on the chin with considerable force while shifting the chin back and forth sidewise and slightly up and down by the thumb and forefinger, as illustrated in FIG. 7, until the patient's jaw muscles tire and his flexive resistance to centric occlusion is substantially eliminated for an interval. The ture centric relation of both condile heads relative to the sockets in the cranium concurrently is readily recognizable by the experienced dentist. Hence the operation is continued with the force mentioned while the lower jaw is gradually permitted to approach closely full centric occulsion of the teeth. It is then held in this condition and the bite tray, or one frame thereof, loaded with proper paste, is inserted between the teeth. This insertion is done by one hand; for example, the right if the left hand is holding the jaws in centric relation, or vice versa. However, with the greater length between the frame members and the rearward edge of the tabs in the prior structure, it is difficult to hold the tray in proper position, parallel to the occlusion plane of the centric jaws while holding the jaws in centric relation. As the lower jaw is held in centric relation by the thumb and forefinger of one hand of the dentist, and with the jaw almost in closed position, the rear of the knuckle of the thumb of the holding hand is about in the plane of occlusion of the teeth. In this position, the present frame, in loaded condition, is inserted by the other hand between the teeth, which now are separated just enough to permit insertion of the charged frame, and the tabs are allowed to rest on and be guided by the rear knuckle of the thumb of the holding hand. The jaws can be held in proper position while the rear knuckle of the thumb is in this position substantially in the plane of occulsion. With the loaded tray inserted between the teeth and held by the said other hand with the tabs resting on the knuckle of the thumb of the holding hand, the jaws are closed while the thumb and forefinger of the holding hand maintain the upward rearward pressure and cause the closure to occur in true centric relation. In this manner, due to the shorter handle, an accurate bite impression in true centric relation of the jaws is obtained. The paste offers little resistance to occlusion of the teeth. The felted bib preferably is less than 0.003 inches thick so that the jaws can be closed to within 0.002 of an inch of final position before any appreciable resistance developes. The resistance is so slight during final closure that it does not destroy the centric relation. Such registrations enable the dentist to mount the casts of the upper and lower arches on the articulator in a true centric relation so that the partial plates or full plates can be produced with assurance that they will fit and function properly when placed in the mouth of the patient.

Having thus described my invention, I claim:

1. A bib and bite frame combination for introducing bite registration material between the occlusal surfaces of the teeth comprising:

a frame of stiff, resilient wire, and having an elongated buccal frame member, an elongated lingual frame member spaced laterally therefrom and generally parallel thereto, and a transverse end frame member at, and connecting, one end of the buccal frame member to one end of the lingual frame member, and disposed at about a right angle to the lengths of said buccal and lingual frame members;

said buccal and lingual frame members extending forwardly from the end frame member;

said buccal frame member having at its forward end an integral forwardly extending handle, said handle joining the buccal frame member by an integral curvilinear portion of said wire which is convex inwardly from the buccal frame member and handle, and said lingual frame member having its forward end free;

a bib comprising a strip of thin, flexible, soft material and elongated, straight, channel members open at both ends and connected to the lateral margins of the strip, respectively;

each channel member being shaped throughout its length to accommodate near its bottom an associated one of said lingual and buccal frame members in a position extending endwise of the channel member, and each channel member having resilient side walls with portions defining a radially open restricted entry passage which is coextensive endwise with the channel member, the ends of the flexible strip being free;

each channel member being resiliently resistant to flexure transversely of its longitudinal axis so as to conform in contour, in a direction transversely of the frame, with its associated frame member, and being composed of resiliently distortable, self-restoring elastomeric material of which the resiliency and self-restoring characteristics are such as to provide for clamping engagement of the channel members with buccal and lingual frame members, respectively, when the buccal and lingual frame members are inserted radially thereinto through the radial entry passage;

characterized in that the length of said lingual frame member, measured from its free end to the end frame member, is materially shorter than the buccal frame member, measured from said end frame member to the juncture of said buccal frame member and said curvilinear portion, and at least one of said channel members is longer than the lingual frame member.

2. The structure according to claim 1 wherein the bib is about as long as the buccal frame member.

3. The structure according to claim 1 wherein said length of the lingual frame member is from about one half to two thirds of said length of the buccal frame member.

4. The structure according to Claim 1 wherein said length of the lingual frame member is at least one and one half times said length of the lingual frame member.

5. The structure according to Claim 1 further characterized in that:
    said curvilinear wire portion is a gradual uninterrupted intermediate curve merging at points of tangency with the adjacent ends, respectively, of the handle and the buccal frame member;
    the curvature of said curvilinear wire portion is sufficiently gradual so that one of said channel members, when installed on the buccal frame member and said curvilinear portion, remains in conformance in contour transversely of the frame to the buccal frame member and said curvilinear portion; and
    said one of the channel members can be slid endwise of the attached associated buccal frame member in a direction away from the end frame member, and as it is so slid, can conform in said contour to said curvilinear portion and the handle adjacent thereto.

6. The structure according to claim 1 wherein the ratio of said length of the lingual frame member to said length of the buccal frame member is substantially 0.6.

7. The structure according to claim 1 wherein the ratio of length of handle, measured from that end of the handle joining said curvilinear portion to the opposite end of the handle, to said length of buccal frame member is about 0.70.

8. A bite frame according to claim 1, wherein
    said handle has a large rest tab at the end opposite the buccal frame member, and the length of the handle between the rearmost end of the tab and the forwardmost end of the buccal frame member is from about one fourth to one third of the length of the buccal frame member.

* * * * *

UNITED STATES PATENT OFFICE
CERTIFICATE OF CORRECTION

PATENT NO. : 3,987,548
DATED : October 26, 1976
INVENTOR(S) : Russell J. Jones

It is certified that error appears in the above-identified patent and that said Letters Patent are hereby corrected as shown below:

Col. 5, line 22, after "the" read --rearmost of the--;
line 29, "of times" should read --oftimes--.
Col. 6, line 17, for "served" read --severed--.
Col. 7, line 26, for "ture" read --true--.

Signed and Sealed this

Twenty-second Day of February 1977

[SEAL]

Attest:

RUTH C. MASON
Attesting Officer

C. MARSHALL DANN
Commissioner of Patents and Trademarks